US010050476B2

United States Patent
Strommer et al.

(10) Patent No.: US 10,050,476 B2
(45) Date of Patent: Aug. 14, 2018

(54) RECHARGEABLE IMPLANTABLE CARDIOVERTER DEFIBRILLATOR

(71) Applicant: NewPace Ltd., Caesarea (IL)

(72) Inventors: Gera Strommer, Haifa (IL); Avraham Broder, Petach Tikva (IL)

(73) Assignee: NewPace Ltd., Caesarea (IL)

( * ) Notice: Subject to any disclaimer, the term of this patent is extended or adjusted under 35 U.S.C. 154(b) by 248 days.

(21) Appl. No.: 15/151,656

(22) Filed: May 11, 2016

(65) Prior Publication Data

US 2016/0331980 A1      Nov. 17, 2016

Related U.S. Application Data

(60) Provisional application No. 62/159,986, filed on May 12, 2015.

(51) Int. Cl.
*H02J 50/12*     (2016.01)
*A61N 1/378*     (2006.01)
(Continued)

(52) U.S. Cl.
CPC ............ *H02J 50/12* (2016.02); *A61N 1/3756* (2013.01); *A61N 1/3787* (2013.01); *A61N 1/37223* (2013.01); *A61N 1/3956* (2013.01); *A61N 1/3968* (2013.01); *H02J 7/025* (2013.01); *H02J 7/027* (2013.01); *H02J 50/10* (2016.02); *H02J 50/80* (2016.02); *H02J 50/90* (2016.02); *H04B 5/0037* (2013.01); *A61N 1/0504* (2013.01); *A61N 1/0563* (2013.01); *A61N 1/36507* (2013.01); *A61N 1/37229* (2013.01);
(Continued)

(58) Field of Classification Search
CPC .................................. H02J 50/12; H02J 50/80

USPC ........................................................... 607/5
See application file for complete search history.

(56) References Cited

U.S. PATENT DOCUMENTS 6,647,292 B1    11/2003   Bardy et al.
6,721,597 B1    4/2004    Bardy et al.
(Continued)

FOREIGN PATENT DOCUMENTS

EP        2510973 A2      10/2012

OTHER PUBLICATIONS

Extended European Search Report dated Oct. 6, 2016 for European Patent Application No. 16001061.7 (6 Pages).

*Primary Examiner* — Nadia A Mahmood
(74) *Attorney, Agent, or Firm* — Brown Rudnick LLP (57) ABSTRACT

Rechargeable implantable cardioverter defibrillator including a hermetically sealed can and at least one lead, coupled with the hermetically sealed can, the hermetically sealed can including at least one high voltage capacitor, an electronic circuit, coupled with the high voltage capacitor and a rechargeable battery, coupled with the electronic circuit and the high voltage capacitor, an outer surface of the hermetically sealed can including an active section and a non-active section, the non-active section being electrically insulated from the active section, wherein a surface area of the active section acts as at least one of an electrode with the lead for forming an electric shock vector for applying a high voltage shock and a sensor for sensing electrical activity and wherein a surface area of the non-active section acts as at least one antenna for transmitting and receiving information wirelessly while also receiving electromagnetic energy to inductively charge the rechargeable battery.

26 Claims, 5 Drawing Sheets

(51) Int. Cl.
| | |
|---|---|
| *H02J 7/02* | (2016.01) |
| *A61N 1/39* | (2006.01) |
| *A61N 1/372* | (2006.01) |
| *H02J 50/10* | (2016.01) |
| *H02J 50/80* | (2016.01) |
| *H02J 50/90* | (2016.01) |
| *A61N 1/375* | (2006.01) |
| *H04B 5/00* | (2006.01) |
| *H02J 7/34* | (2006.01) |
| *A61N 1/05* | (2006.01) |
| *A61N 1/365* | (2006.01) |

(52) U.S. Cl.
CPC ............ *A61N 1/395* (2013.01); *A61N 1/3962* (2013.01); *H02J 7/345* (2013.01)

(56) References Cited

U.S. PATENT DOCUMENTS

| | | | |
|---|---|---|---|
| 7,363,083 | B2 | 4/2008 | Bardy et al. |
| 7,389,138 | B2 | 6/2008 | Wagner et al. |
| 7,684,864 | B2 | 3/2010 | Olson et al. |
| 7,792,588 | B2 | 9/2010 | Harding |
| 7,894,894 | B2 | 2/2011 | Stadler et al. |
| 7,991,467 | B2 | 8/2011 | Markowitz et al. |
| 8,260,415 | B2 | 9/2012 | Donofrio |
| 8,290,593 | B2 | 10/2012 | Libbey et al. |
| 8,359,094 | B2 | 1/2013 | Bonner et al. |
| 8,452,404 | B1 | 5/2013 | Fischell et al. |
| 8,483,841 | B2 | 7/2013 | Sanghera et al. |
| 8,512,254 | B2 | 8/2013 | Donofrio |
| 8,644,926 | B2 | 2/2014 | Ostroff et al. |
| 8,700,174 | B2 | 4/2014 | Skelton et al. |
| 8,718,760 | B2 | 5/2014 | Bardy et al. |
| 8,744,572 | B1 | 6/2014 | Greenhut et al. |
| 2002/0013613 | A1 | 1/2002 | Haller et al. |
| 2004/0172066 | A1* | 9/2004 | Wagner ............... A61N 1/3962 607/4 |
| 2008/0183247 | A1 | 7/2008 | Harding |
| 2011/0093051 | A1 | 4/2011 | Davis et al. |
| 2011/0106200 | A1 | 5/2011 | Ziegler |
| 2012/0276856 | A1 | 11/2012 | Joshi et al. |
| 2013/0304139 | A1 | 11/2013 | Musley et al. |
| 2014/0277245 | A1 | 9/2014 | Lu et al. |
| 2014/0304773 | A1 | 10/2014 | Woods et al. |

* cited by examiner

RECHARGEABLE IMPLANTABLE CARDIOVERTER DEFIBRILLATOR

CROSS-REFERENCE TO RELATED APPLICATION

This application claims the benefit of, and priority to, provisional U.S. patent application Ser. No. 62/159,986, filed May 12, 2015, the entire contents of which are incorporated herein by reference.

FIELD OF THE DISCLOSED TECHNIQUE

The disclosed technique relates to implantable cardioverter defibrillators (herein abbreviated ICD), in general, and to systems and methods for constructing and operating rechargeable ICDs, in particular.

BACKGROUND OF THE DISCLOSED TECHNIQUE

An arrhythmia is a medical condition in which there exists a problem with the rate or rhythm of the heartbeat usually due to abnormal electrical activity in the heart. More specific types of arrhythmia include when the heart beats too fast (known as tachycardia), too slow (known as bradycardia) or with an irregular rhythm (known as cardiac fibrillation). Two general devices are known in the art for helping people who experience arrhythmias. One is known as a pacemaker, the other is known as an implantable cardioverter defibrillator (herein abbreviated ICD). Pacemakers are implantable devices which continuously measure the heartbeat and electrical activity in the heart. Pacemakers can detect irregularities in the heartbeat, i.e. arrhythmias, and are programmed to provide electrical signals to the heart to restore its normal beating rhythm. ICDs are similar to pacemakers and include similar components but differ slightly from pacemakers in that they include a power source, electronics, electrical leads as well as at least one capacitor. The difference between an ICD and a pacemaker is that an ICD can deliver a high voltage electric shock to the heart to terminate an otherwise potentially fatal cardiac tachyarrhythmia, such as ventricular fibrillation (herein abbreviated VF). A pacemaker is generally limited to treating less severe arrhythmias such as bradyarrhythmias which can be treated with a significantly lower voltage electric impulse. The presence of at least one high voltage capacitor in an ICD accounts for its difference in function from a pacemaker as the at least one high voltage capacitor enables a significantly higher voltage electrical shock to be built up and delivered as higher voltage energy to the heart. In the case of VF, the function of an ICD is to send the heart an electrical shock in order to prevent cardiac arrest, i.e., aborted sudden death; this is highly important and could be a matter of life or death. The electrical energy required for the electrical shock is built up and stored in the at least one high voltage capacitor. ICDs exist as standalone devices yet are also manufactured having the functionality of a pacemaker. In addition, cardiac resynchronization therapy defibrillators (herein abbreviated as CRT-D), which are similar to ICDs, may include an additional electrode to enable simultaneous pacing of both the right and left ventricles of the heart.

Figure 1A:
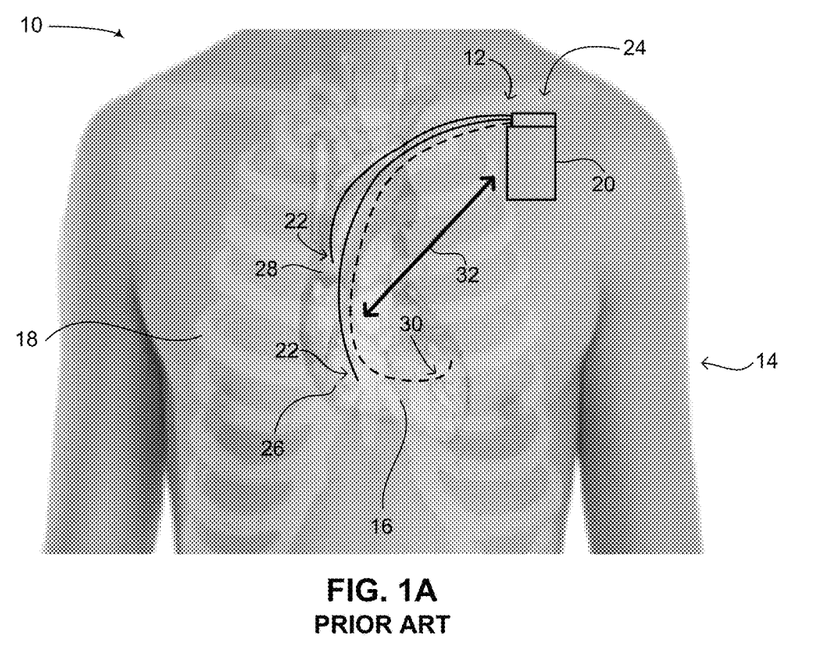
FIG. 1A is a schematic illustration of an ICD implanted in a patient, as is known in the art.

Reference is now made to FIG. 1A, which is a schematic illustration of an ICD implanted in a patient, generally referenced 10, as is known in the art. As shown in FIG. 1A, an ICD 12 is implanted in a patient 14, having a heart 16 and a ribcage 18. ICD 12 includes two main components, a single can 20 and electrical leads 22. Can 20 can also be referred to as a canister or housing. Can 20 includes a power source (not shown), such as a battery, a high voltage capacitor, as well as an electronic circuit (not shown) for monitoring the electrical activity in the heart and for providing electrical signals to the heart when aberrant rhythms of the heart are detected. Can 20 is usually implanted in patient 14 via a surgical procedure on his left side adjacent to and below the clavicle bone (also known as the collarbone), as shown by an arrow 24 in FIG. 1A. Electrical leads 22 are coupled with the electronic circuit in can 20 at one end and are coupled with heart 16 at the other end, the electrical leads being inserted through the subclavian vein (not shown) and the vena cava (not shown). Electrical leads 22 are typically implanted in patient 14 by inserting them percutaneously through his vena cava (not shown) and into heart 16. Once attached to heart 16, they are coupled with can 20. Electrical leads 22 are usually flexible and provide electrical signals of heart 16 to the electronic circuit in can 20 and are used to deliver a high voltage and high energy shock from the electronic circuit to heart 16 in the case of VF. Typically, electrical leads 22 are implanted in right ventricle 26 and right atrium 28 of heart 16.

As mentioned above, ICDs, similar to pacemakers, constantly monitor the rate and rhythm of the heart and deliver therapies to the heart by way of an electrical shock. In the case of an ICD, electrical shocks are provided to the heart when the measured electrical activity of the heart exceeds a preset number. State of the art ICDs can distinguish different types of aberrant electrical activity in the heart, such as VF, when the heart contracts irregularly, versus ventricular tachycardia (herein abbreviated VT), when the heart beats regularly but significantly faster than normal. In the case of VT, such ICDs may send electrical signals to the heart to try and pace the heart faster than its intrinsic heart rate in an attempt to stop the tachycardia before it progresses to VF. This technique is known in the art as fast-pacing, overdrive pacing or anti-tachycardia pacing (herein abbreviated ATP). As is known to workers skilled in the art, ATP is only effective if the underlying rhythm of the heart is ventricular tachycardia. State of the art ICDs use a combination of various methods to determine if received electrical signals from the electrical leads represent a normal rhythm of the heart, ventricular tachycardia or ventricular fibrillation. It is noted that the placement of an ICD in the body of a patient is similar to that of a pacemaker, however in the case of a CRT-D device, the electrical leads can also be implanted in the left side of the heart via the coronary sinus (not shown) of the heart. This is shown in FIG. 1A as an electrical lead 30, denoted by a dashed line. In addition, is it noted that state of the art ICDs exist in which the electrical leads of an ICD are not inserted into the heart but are positioned subcutaneously above or around the heart. This is shown below in FIGS. 1B and 1D. Such ICDs provide improved safety to a patient since the insertion of the electrical leads of the ICD does not involve any intervention with the heart.

Pacemakers and ICDs with intravascular leads, as shown in FIG. 1A, are advantageous in that the electrical leads used for sensing arrhythmias as well as delivering electrical shocks and impulses to the heart are placed directly in the heart (i.e., hence intravascularly). Such a placement of the electrical leads allows for a significantly high signal-to-noise ratio (herein abbreviated SNR) such that aberrant electrical activity detected in the heart is in fact aberrant electrical activity of the heart and not electrical activity coming from another source of electrical activity in the body near the heart or from a source outside the body generating an electric field. Also, the closeness of the electrical leads to the chambers of the heart enables a generally lower voltage to be applied to the heart for either pacing it or for treating VT or VF via high voltage electrical shocks. Such pacemakers and ICDs however are disadvantageous in that major surgery is required to implant the can in the body and the electrical leads in the vasculature of the heart. This disadvantage is true of intravascular ICDs as well as the entire device must be implanted in the vasculature of the patient. Furthermore, when the energy of the battery is depleted, or if there is a problem with the electrical leads placed in the heart, the patient must undergo further surgery to either replace the entire can or to have new electrical leads placed in the heart. Pacemakers and ICDs having cans with replaceable and/or rechargeable batteries are currently not on the market, thus when the battery of such devices is depleted, the entire can of the device (pacemaker or ICD) must be replaced.

In the past decade, there has been a general trend in surgery and implantable medical devices to reduce the amount of invasiveness of either the surgery involved or the positioning of the implantable medical device in the body of a patient. For example, in the field of ICDs, medical device companies have begun researching and developing subcutaneous ICDs which are to be placed under the skin and around the heart, thereby significantly reducing the invasiveness of an implanting procedure and the actual positioning of the ICD in the body of the patient. One of the reasons for this trend in ICDs is that many health-related issues have occurred with the intravascular and intracardiac leads used in prior art ICDs, including the recall of such leads. Intravascular and intracardiac leads move a tremendous amount within the heart as it beats during the lifespan of a prior art ICD. With an average of 70 movements per minute over the course of seven years, an intravascular lead may move over 250 million times. These leads thus require a very high durability due to the continuous movement of these leads within the heart and can wear and break over time, causing serious problems to the patient, including patient death. Major companies in this field include Boston Scientific, Cameron Health (acquired by Boston Scientific), Medtronic and St. Jude Medical. Of these companies, only Cameron Health has an actual subcutaneous ICD device in the market.

Figure 1B:
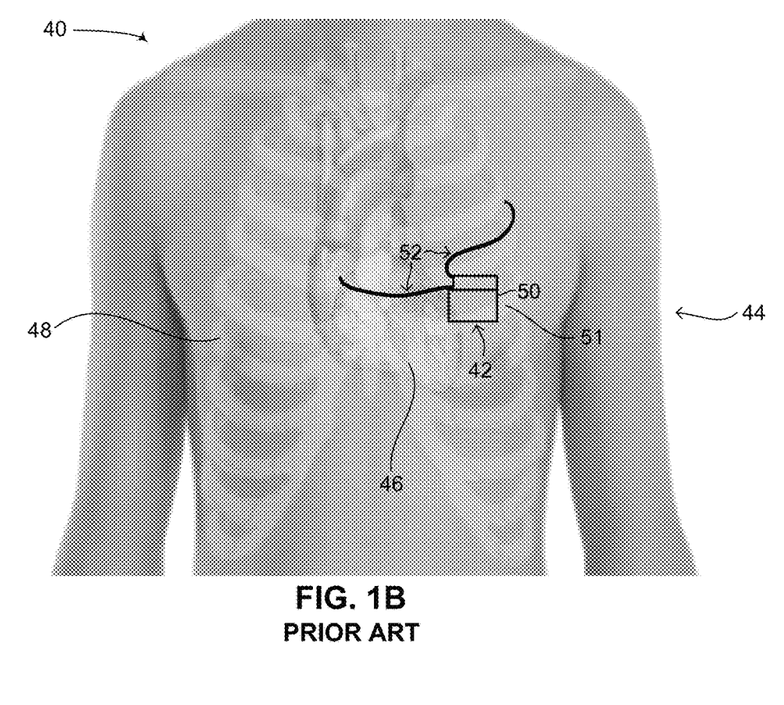
FIG. 1B is a schematic illustration of a first subcutaneous ICD implanted in a patient, as is known in the art.

Reference is now made to FIG. 1B, which is a schematic illustration of a first subcutaneous ICD implanted in a patient, generally referenced 40, as is known in the art. A patient 44 is shown, having a heart 46 and a ribcage 48. A subcutaneous ICD 42 in placed under the skin near the heart. Subcutaneous ICD 42 includes a can 50 and electrical leads 52, each respectively similar to can 20 (FIG. 1A) and electrical leads 22 (FIG. 1A). Can 50 can also be referred to as a canister. Can 50 is usually positioned under the skin around a fifth left rib 51, near the heart (i.e., laterally to the heart), whereas electrical leads 52 are positioned around heart 46. Usually a first electrical lead is positioned anterior to heart 46 whereas a second electrical lead is positioned posterior to heart 46, thus creating an electrical shock vector between the two electrical leads via heart 46. Subcutaneous ICD 42 thus also has a can and leads configuration, similar to pacemaker 10 (FIG. 1A).

Subcutaneous ICD 42 is advantageous over an ICD with intravascular leads and an intravascular ICD in that major surgery is not involved in its placement and improved safety is provided to the patient since the insertion of the electrical leads of the ICD does not involve any intervention with the heart or puncturing of a blood vessel. Replacing can 50 or replacing electrical leads 52 if they are faulty is also simpler in that only percutaneous surgery is involved. However, since subcutaneous ICD 42 and its electrical leads are not placed in the vasculature of the heart, electrical leads 52 may have a significantly lower SNR and thus the electric circuit (not shown) in can 50 may have a harder time differentiating between electrical activity of the heart and what is known in the field as extra-cardiac oversensing or extra-cardiac noise (i.e., electrical activity sensed from non-cardiac muscles around the heart and electrical activity coming from sources outside the patient). This difficulty in differentiating between true electrical activity of the heart and extra-cardiac oversensing can lead to subcutaneous ICD 42 delivering shocks to the heart when it doesn't need it and also failing to deliver shocks to the heart when it does need it. In addition, since electrical leads 52 are not placed directly in heart 46, a higher voltage must be applied to the leads for treating VT or VF via electrical shocks as compared with conventional ICDs (as in FIG. 1A) in which its leads are placed intravascularly directly in the heart. The higher voltage requires a higher level of energy. The higher level of energy thus requires a larger can volume since the can requires a larger battery and larger high voltage capacitors to provide the higher energy requirements. The can and leads configuration of subcutaneous ICD 42 may also cause discomfort to patient 44, especially considering that the rigid outer surface of can 50 is placed directly on ribcage 50 where humans in general do not have a lot of excess skin or fat tissue in this particular region of the body to cushion can 50. A further disadvantage of a subcutaneous ICD is that due to its placement in a patient, many sensory and motor nerves are located between the electrical leads. Any stimulation generated between the electrical leads for the heart will be felt by the patient as both muscle contractions (i.e., from the motor nerves) and pain (i.e., from the sensory nerves). This is much less of a concern for an ICD with intracardiac leads, especially when stimulation is generated between the leads in the heart, as the electric field generated is essentially limited to the area of the heart and does not cause muscle contractions or the sensation of pain around the heart. If it for this reason that subcutaneous ICDs generally do not provide a pacing function.

Figure 1C:
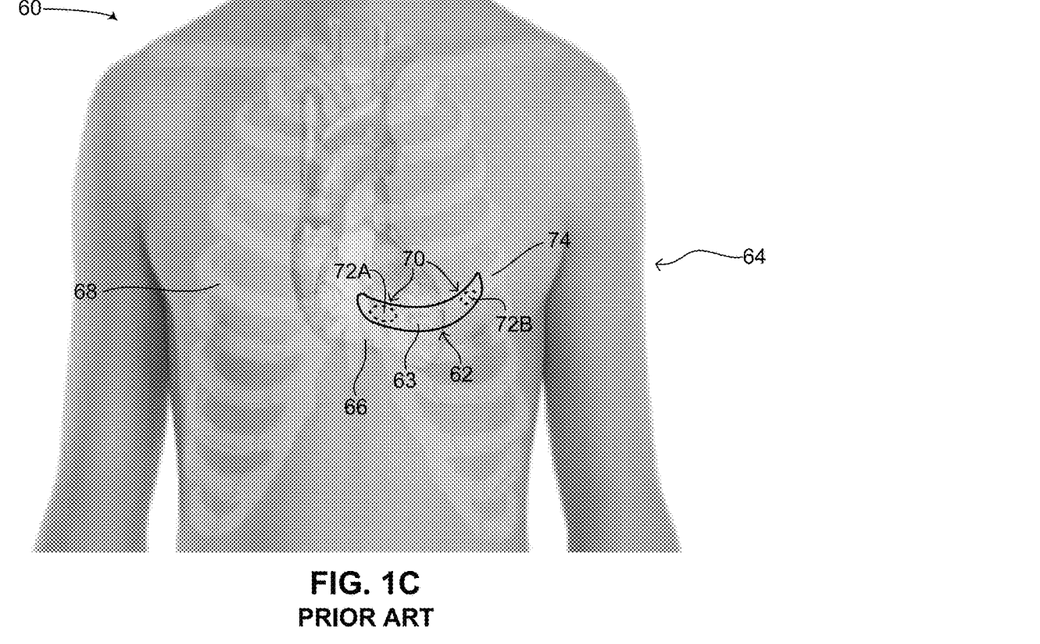
FIG. 1C is a schematic illustration of a second subcutaneous ICD implanted in a patient, as is known in the art.

Some of the concerns with subcutaneous ICD 42 have been mitigated by medical device companies using a different configuration for subcutaneous ICDs, such as a curved configuration. Reference is now made to FIG. 1C, which is a schematic illustration of a second subcutaneous ICD implanted in a patient, generally referenced 60, as is known in the art. A patient 64 is shown having a heart 66 and a ribcage 68. A subcutaneous ICD 62 in placed under the skin near the heart. Subcutaneous ICD 62 includes a housing 63. Housing 63 includes a plurality of surface electrodes 70, an electric circuit (not shown), a battery (not shown) and at least one high voltage capacitor (not shown), similar to the elements found in subcutaneous ICD 42 (FIG. 1B). Housing 63 has a curved configuration, being thin, narrow and flexible, similar to a patch, bandage or plaster and shaped to fit around a patient's rib. Plurality of surface electrodes 70 are positioned on one side of housing 63, giving subcutaneous ICD 62 a specific directionality. As shown in FIG. 1C, a first surface electrode 72A and a second surface electrode 72B are placed on an inner side of housing 63, facing towards the body (not labeled) of patient 64. As compared with subcutaneous ICD 42, subcutaneous ICD 62 does not have any electrical leads. Instead first surface electrode 72A and second surface electrode 72B are used to both sense electrical activity of heart 66 as well as apply electrical shocks to heart 66. Plurality of surface electrodes 70 thus function as electrical leads.

Housing 63 is usually positioned under the skin around a fifth left rib 74, near the heart. Since housing 63 is flexible, it is usually wrapped around fifth left rib 74, or near it, following the contours of ribcage 68 and partially wrapping around heart 66. A proximal end (not labeled) of housing 63 may be anterior to heart 66 and a distal end (not labeled) of housing 63 may be posterior to heart 66. An electrical shock vector is thus created between plurality of surface electrodes 70 via heart 66. It is noted that housing 63 is usually made of metal and can also function as a sensor or electrical lead. Housing 63 is thus also referred to in the art as an active can. In such a configuration, one of the surface electrodes can be used to sense electrical activity whereas the other surface electrode can be used with housing 63 to create an electrical shock vector. Subcutaneous ICDs having a curved configuration are known in the art, such as U.S. Pat. No. 6,647,292 B1 to Bardy et al., assigned to Cameron Health, entitled "Unitary subcutaneous only implantable cardioverter-defibrillator and optional pacer." Other examples include the following patents: U.S. Pat. No. 7,363,083 B2, U.S. Pat. No. 8,718,760 B2 (all assigned to Cameron Health Inc.) and U.S. Pat. No. 7,684,864 B2 (assigned to Medtronic Inc.).

Whereas subcutaneous ICD 62 may be more comfortable for a patient than subcutaneous pacemaker 42 (FIG. 1B) due to its flexible thin shape and slightly reduced invasiveness since only a single element needs to be implanted in patient 64, surgery is still required to replace a dead battery in subcutaneous ICD 62. In addition, subcutaneous ICD 62 may suffer the same SNR issues that accompany subcutaneous ICD 42 in terms of differentiating true cardiac electrical activity compared to extra-cardiac oversensing. In addition, as mentioned above subcutaneous ICD 62 has a particular directionality and must be placed in a specific orientation to function properly in patient 64.

Figure 1D:
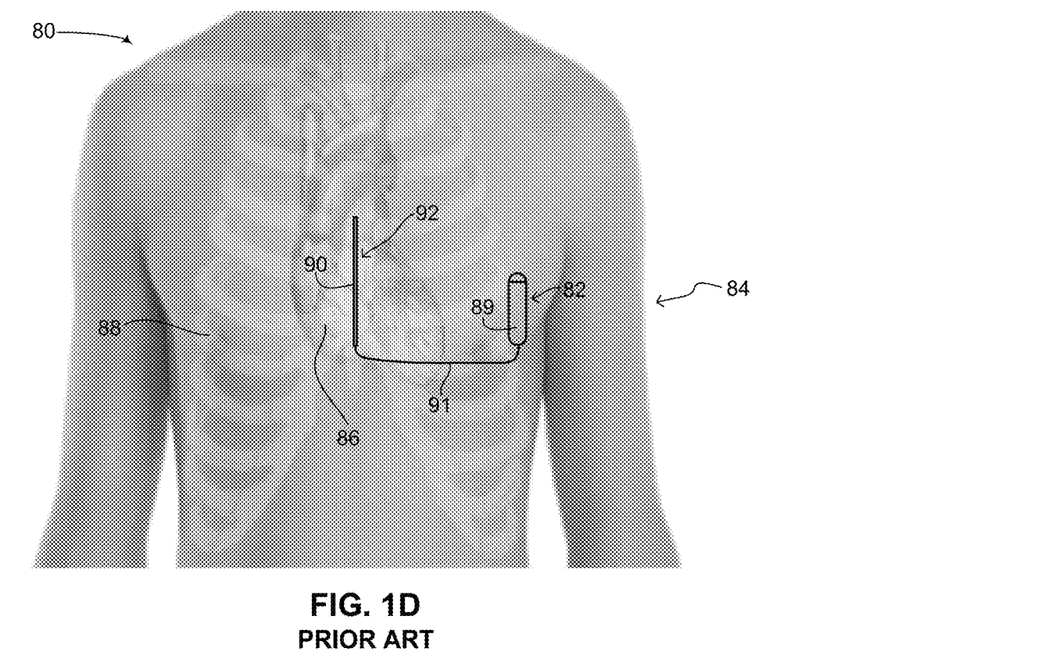
FIG. 1D is a schematic illustration of a third subcutaneous ICD implanted in a patient, as is known in the art.

Reference is now made to FIG. 1D, which is a schematic illustration of a third subcutaneous ICD implanted in a patient, generally referenced 80, as is known in the art. A patient 84 is shown, having a heart 86 and a ribcage 88. A subcutaneous ICD 82 in placed under the skin just outside ribcage 88 near the heart. Subcutaneous ICD 82 includes a can 89 and an electrical lead 91, each respectively similar to can 20 (FIG. 1A) and electrical leads 22 (FIG. 1A). Can 89 and electrical lead 91 are coupled by a wire 90. Electrical lead 91 is positioned over a sternum 92 of ribcage 88, anterior to heart 86. Can 89 is an active can and substantially acts as an electrode and secondary electrical lead. An electrical shock vector can thus be generated between can 89 and electrical lead 91. Like in FIG. 1B, subcutaneous ICD 82 has a can and leads configuration, similar to ICD 12 (FIG. 1A). Subcutaneous ICDs having a can and leads configuration are known in the art, such as described in U.S. Pat. No. 6,721,597 B1 to Bardy et al., assigned to Cameron Health, Inc., entitled "Subcutaneous only implantable cardioverter defibrillator and optional pacer." Other examples include the following patents and patent applications: U.S. Pat. No. 8,483,841 B2, U.S. Pat. No. 8,644,926 B2 (all assigned to Cameron Health Inc.), U.S. Pat. No. 8,260,415 B2, U.S. Pat. No. 8,512,254 B2, U.S. Pat. No. 8,359,094 B2, U.S. Pat. No. 7,894,894 B2 (all assigned to Medtronic Inc.) and EP 2 510 973 A1 (applicant Cardiac Pacemakers Inc.).

In general each one of cans 20 (FIG. 1A), 50 (FIG. 1B) and 89 (FIG. 1D) is made from metal and is hermetically sealed to prevent bodily fluids from entering therein. The cans thus form Faraday cages. In some prior art ICDs as explained above, the can is an active can, meaning it can conduct electricity and can be used in conjunction with at least one electrical lead for generating a shock vector through the heart. In FIG. 1A for example, this is shown schematically via an arrow 32. On the market ICDs are generally one time use devices in that when their power source, such a battery, is diminished, the can of the device which houses the battery must be completely replaced. Since replacing the can requires surgery to remove the old can and insert a new can, there is a desire to minimize the number of times the can must be replaced over the lifetime of a patient as surgical intervention increases various associated risks (e.g., infection, muscle tissue weakening and the like). In this respect, ICDs are designed with power sources large enough to last on average between 5-7 years in a patient. Since the power source substantially provides electrical charge, most significantly for dealing with VT and VF, there is a direct correlation between the size of an ICD and the amount of charge its battery can store. An increase in battery life of the can is thus directly correlated to an increase in physical size of the ICD, in order to accommodate a large enough power source to last 5-7 years. It is noted that the actual length of time an ICD lasts depends on each particular patient and the actual activity of their heart. An ICD in general stores enough electrical charge to provide around 100 to possibly 200 electrical shocks for dealing with VT and VF. Therefore an ICD may last less than or more than 5-7 years depending on how frequently the ICD must provide high energy electrical shocks when dealing with arrhythmias of the heart of the patient.

ICDs are known in the art as previously mentioned. Further examples include ICDs as disclosed in the following US patents and published US patent applications: U.S. Pat. No. 7,389,138 to Wagner et al., U.S. Pat. No. 7,792,588 to Harding, U.S. Pat. No. 7,991,467 to Markowitz et al., U.S. Pat. No. 8,290,593 to Libbey et al., U.S. Pat. No. 8,452,404 to Fischel) et al., U.S. Pat. No. 8,700,174 to Skelton et al., US 2002/0013613 to Haller et al., US 2004/0172066 to Wagner et al., US 2008/0183247 to Harding, US 2011/0093051 to Davis et al., US 2011/0106200 to Ziegler et al., US 2012/0276856 Joshi et al. and US 2014/0304773 to Woods et al.

SUMMARY OF THE DISCLOSED TECHNIQUE

It is an object of the disclosed technique to provide a novel method and system for a rechargeable ICD which includes at least one antenna and which can be recharged wirelessly. In accordance with the disclosed technique, there is thus provided a rechargeable ICD including a hermetically sealed can and at least one lead. The hermetically sealed can includes at least one high voltage capacitor, an electronic circuit and a rechargeable battery. The outer surface of the hermetically sealed can includes an active section and a non-active section. The lead is coupled with the hermetically sealed can. The electronic circuit is coupled with the high voltage capacitor and the rechargeable battery is coupled with the electronic circuit and the high voltage capacitor. The non-active section is electrically insulated from the active section. A surface area of the active section acts as at least one of an electrode with the lead for forming an electric shock vector for applying a high voltage shock and a sensor for sensing electrical activity. A surface area of the non-active section acts as at least one antenna for transmitting and receiving information wirelessly while also receiving electromagnetic (EM) energy to inductively charge the rechargeable battery.

In accordance with another aspect of the disclosed technique, there is thus provided a rechargeable ICD including a hermetically sealed can and at least one lead. The hermetically sealed can includes at least one high voltage capacitor, an electronic circuit and a rechargeable battery. An outer surface of the hermetically sealed can includes an active section, a non-active section and an isolator. The lead is coupled with the hermetically sealed can. The electronic circuit is coupled with the high voltage capacitor and the rechargeable battery is coupled with the electronic circuit and the high voltage capacitor. The isolator is coupled with the active section and the non-active section and is for electrically insulating the active section from the non-active section. A surface area of the active section acts as at least one of an electrode with the lead for forming an electric shock vector for applying a high voltage shock and a sensor for sensing electrical activity. A surface area of the non-active section acts as at least one antenna for transmitting and receiving information wirelessly while also receiving EM energy to inductively charge the rechargeable battery.

In accordance with a further aspect of the disclosed technique, there is thus provided a rechargeable ICD including an active section and a non-active section. The active section includes at least one high voltage capacitor, an electronic circuit and a rechargeable battery. The electronic circuit is coupled with the high voltage capacitor and the rechargeable battery is coupled with the electronic circuit and the high voltage capacitor. The non-active section is electrically insulated from the active section and forms a hermetically sealed can with the active section. A surface area of the active section acts as at least one of an electrode for forming an electric shock vector for applying a high voltage shock and a sensor for sensing electrical activity. A surface area of the non-active section acts as at least one antenna for transmitting and receiving information wirelessly while also receiving EM energy to inductively charge the rechargeable battery.

In accordance with another aspect of the disclosed technique, there is thus provided a rechargeable ICD including a hermetically sealed can and at least one lead. The hermetically sealed can includes at least one high voltage capacitor, an electronic circuit, a rechargeable battery and at least one antenna. The lead is coupled with the hermetically sealed can. The electronic circuit is coupled with the high voltage capacitor and the rechargeable battery is coupled with the electronic circuit and the high voltage capacitor. The antenna can wirelessly receive EM energy for inductively charging the rechargeable battery. The antenna can wirelessly transmit signals indicative of a status of the rechargeable ICD to an external device and can wirelessly receive signals from a programmer for programming the electronic circuit.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a novel rechargeable ICD which includes at least one internal antenna and which can be recharged wirelessly. The rechargeable ICD can is designed to encapsulate a relatively small battery, thus significantly reducing the size of the can of the ICD. However since the small battery can be recharged, even though less electrical charge is stored on the battery, due to its ability to be recharged, the life span of the novel rechargeable ICD can be as much as two to three times as long as current prior art non-rechargeable ICDs. The at least one antenna of the disclosed technique enables the rechargeable ICD to communicate information about itself to a portable user device, such as a smartphone or tablet computer. The at least one antenna also enables the rechargeable ICD to receive energy and charge the battery in the can inductively and thus wirelessly. The energy used to recharge the battery in the ICD can be modulated such that a wireless programmer can be used by a physician to program the rechargeable ICD while the rechargeable ICD is being recharged. In one embodiment of the disclosed technique, the can of the rechargeable ICD has an active section and a non-active section. The active section enables the can of the rechargeable ICD to be used as an electrode for creating a high voltage electric shock vector through the heart of a patient. The non-active section enables energy and signals to be transferred wireless to and from the rechargeable ICD without interference while nevertheless keeping a hermetically sealed rechargeable ICD can.

It is noted that the disclosed technique relates to any ICD configuration having a single can and at least one lead in which the can acts as an electrode and in conjunction with the at least one lead is used to generate a high voltage electrical shock vector through the heart. Thus any ICD configuration in which the single can includes all the necessary components for functioning as an ICD, such as a power source, at least one high voltage capacitor and an electronic circuit, such as a processor, is applicable to the disclosed technique. In addition, the at least one lead can be placed intravascularly (i.e., within the heart) or nonvascularly (i.e., external to the heart), such as subcutaneously or percutaneously around the heart. It is also noted that in describing the ICD of the disclosed technique, the term "can" can also refer to the terms "canister," "housing," "compartment" or "body."

Figure 2A:
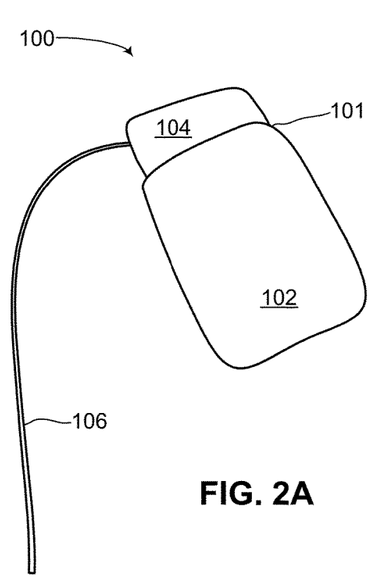
FIG. 2A is a schematic illustration of a rechargeable ICD, constructed an operative in accordance with an embodiment of the disclosed technique.

Reference is now made to FIG. 2A, which is a schematic illustration of a rechargeable ICD, generally referenced 100, constructed an operative in accordance with an embodiment of the disclosed technique. Rechargeable ICD 100 has the general look of known ICDs and includes a can 101 and at least one lead 106. Can 101 encapsulates all the necessary components for an ICD to function as an ICD, including a power source such as a rechargeable battery (not shown), at least one high voltage capacitor (not shown) and an electronic circuit (not shown), such as a processor. Can 101 also includes at least one antenna (not shown) and a charging circuit (not shown). Can 101 includes an active portion 102 and a non-active portion 104. Active portion 102 forms the bulk of can 101 and in general encapsulates the rechargeable battery, the at least one high voltage capacitor, the charging circuit and the electronic circuit. Non-active portion 104 may encapsulate the at least one antenna. At least one lead 106 is coupled with can 101 via non-active portion 104, as shown in FIG. 2A, although at least one lead 106 may also be coupled with active portion 102 via a dielectric feed-thru (not shown). Rechargeable ICD 100 may include a plurality of leads, depending on its functioning. For example, as a pacemaker, only one lead may be necessary yet as a CRT-D, three leads may be necessary. At least one lead 106 includes a shocking coil (not shown) for providing an electrical shock and at least one sensor (not shown) for sensing electrical activity of the heart (not shown). Active portion 102 is a hermetically sealed metal can and substantially acts as an electrode thus enabling a high voltage shock vector to be formed between active portion 102 and at least one lead 106. Active portion 102 can also act as a sensor for sensing electrical activity of the heart. Active portion 102 is active in that it can conduct electricity and substantially forms a Faraday cage. Non-active portion 104 is not active and thus does not form a Faraday cage and therefore enables electromagnetic (herein abbreviated EM) signals to pass there through. Non-active portion 104 may be made from an insulating material such as glass, ceramic or porcelain and is electrically insulated from active portion 102. It is noted that non-active portion 104 can be placed anywhere on the outer surface of active portion 102 and not just in the configuration as shown in FIG. 2A. In addition, non-active portion 104 can take up any portion of the surface area of active portion 102. Non-active portion 104 does not act as an electrode in conjunction with at least one lead 106 like active portion 102 does and is thus transparent to electromagnetic energy. Non-active portion 104 does not create a Faraday cage in contrast to active portion 102, which is substantially a metal can.

Figure 2B:
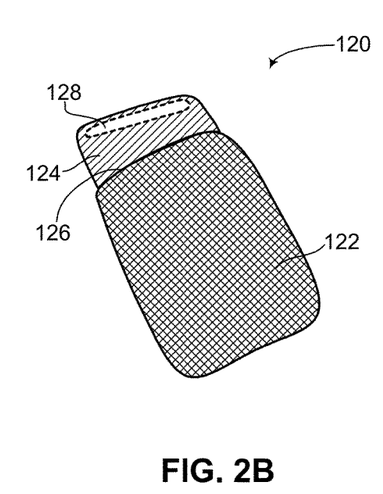
FIG. 2B is a see-through schematic illustration of the rechargeable ICD of FIG. 2A, constructed an operative in accordance with another embodiment of the disclosed technique.

Reference is now made to FIG. 2B, which is a see-through schematic illustration of the rechargeable ICD of FIG. 2A, generally referenced 120, constructed an operative in accordance with another embodiment of the disclosed technique. Rechargeable ICD 120 is shown without the least one lead to keep the figure simple and not cluttered. As shown, the can (not labeled) of rechargeable ICD 120 includes an active portion 122 and a non-active portion 124. Active portion 122 is colored with hatched lines indicating that it is active and can conduct electricity. Non-active portion 124 is not active and thus does not conduct electricity. Since active portion 122 is made from metal and is active, non-active portion 124 must be insulated from active portion 122 otherwise it too may become active. As shown, an insulator 126 is placed between active portion 122 and non-active portion 124 to electrically insulate non-active portion 124 from active portion 122. Insulator 126 can be made from glass, porcelain, ceramic or other known insulator materials. Shown as well in FIG. 2B is at least one antenna 128, located within non-active portion 124. At least one antenna 128 is internal to the can of rechargeable ICD 120, thus enabling the outer surface of rechargeable ICD 120 to remain a smooth, simple shape. In addition, at least one antenna 128 can transmit and receive signals from within non-active portion 124 since non-active portion 124 is not active and does not form a Faraday cage.

Figure 3:
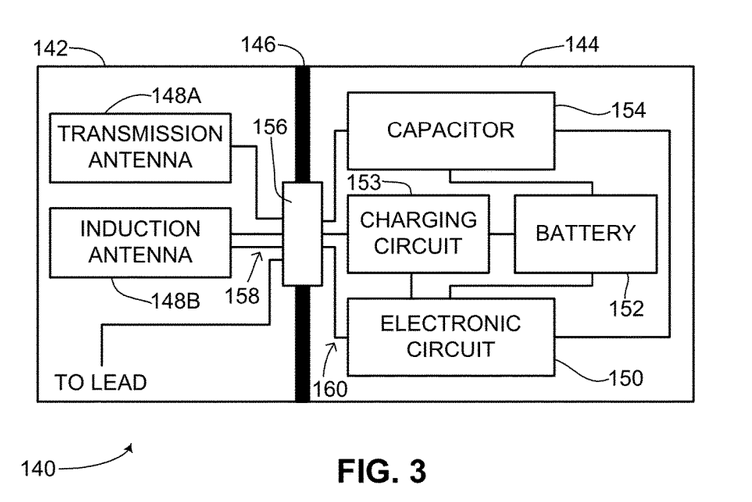
FIG. 3 is a schematic illustration of the internal components of the rechargeable ICD can of FIG. 2A, constructed and operative in accordance with a further embodiment of the disclosed technique.

Reference is now made to FIG. 3, which is a schematic illustration of the internal components of the rechargeable ICD can of FIG. 2A, generally referenced 140, constructed and operative in accordance with a further embodiment of the disclosed technique. As shown, rechargeable ICD can 140 includes a non-active portion 142, an active portion 144 and an insulator 146. Non-active portion 142 is not active and insulator 146 electrically insulates non-active portion 142 from active portion 144. It is noted that insulator 146 may form a part of non-active portion 142 and may be a glass or ceramic compartment forming non-active portion 142. Non-active portion 142 includes a transmission antenna 148A, an induction antenna 148B and at least one lead connection (not shown). Active portion 144 includes an electronic circuit 150, a rechargeable battery 152, a charging circuit 153 and at least one high voltage capacitor 154. Rechargeable battery 152 is coupled with electronic circuit 150, charging circuit 153 and at least one high voltage capacitor 154. At least one high voltage capacitor 154 is coupled with electronic circuit 150. Charging circuit 153 is also coupled with rechargeable battery 152. Transmission antenna 148A is coupled with electronic circuit 150 via a dielectric feed-thru 156. Induction antenna 148B is coupled with charging circuit 153 and electronic circuit 150 via dielectric feed-thru 156. Charging circuit 153 is coupled with dielectric feed-thru 156. At least one high voltage capacitor 154 and electronic circuit 150 are coupled with a lead (not shown) via dielectric feed-thru 156. Dielectric feed-thru 156 enables a plurality of wires 158 from transmission antenna 148A, induction antenna 148B and the at least one lead connection to couple with a plurality of wires 160 from electronic circuit 150, at least one high voltage capacitor 154 and charging circuit 153 while maintaining the hermetic seal of non-active portion 142 and active portion 144 and the electrical insulation as provided by insulator 146. The at least one lead connection (not shown) is for coupling the at least one lead (not shown) of the rechargeable ICD with rechargeable ICD can 140. As mentioned above, the at least one lead connection could be positioned in active portion 144 via another dielectric feed-thru (not shown).

It is noted that electronic circuit 150 can be embodied as a processor. At least one high voltage capacitor 154 is provided with charge via rechargeable battery 152. Electronic circuit 150 receives information about the electrical activity of the heart (not shown) via the lead. If an arrhythmia is detected, then electronic circuit 150 provides a signal to at least one high voltage capacitor 154 to discharge and provide an electric shock via the lead to the heart. As mentioned above, the electric shock vector is provided between the lead and active portion 144 which acts as an electrode. Induction antenna 148B can transmit and receive signals whereas transmission antenna 148A can only transmit signals. In another embodiment of the disclosed technique, transmission antenna 148A and induction antenna 148B are embodied as a single antenna. Transmission antenna 148A can transmit signals from electronic circuit 150 to an external device (not shown), such as a smartphone or tablet computer, to provide diagnostic information about rechargeable ICD can 140 to a user. Induction antenna 148B can transmit signals to a programmer (not shown) for providing diagnostic information about rechargeable ICD can 140 to a physician, such as a cardiologist or electrophysiologist. Induction antenna 148B can also receive signals. Induction antenna 148B can receive EM energy, for example in the form of radio frequency (herein abbreviated RF) energy. The received energy is passed to charging circuit 153 which converts the RF energy into electrical energy that can be used to inductively recharge rechargeable battery 152. Induction antenna 148B can also receive signals from the programmer, which are passed to electronic circuit 150, to change settings and the functioning of rechargeable ICD can 140.

Rechargeable battery 152 can be any known rechargeable battery as used in medical devices, such as a lithium-ion battery. Since rechargeable battery 152 can be recharged, rechargeable battery 152 can be physically smaller and designed to only hold enough electrical charge to charge at least one high voltage capacitor 154 around twenty times and to maintain the functionality of rechargeable ICD can 140 during electrical shocks and between electrical shocks. This may result in rechargeable ICD can 140 being substantially smaller than other ICD cans. In addition, since rechargeable battery 152 can be recharged multiple times, for example hundreds of charge-discharge cycles, rechargeable ICD can 140 may be able to provide up to hundreds of electrical shocks before rechargeable battery 152 can no longer be recharged. Therefore according to the disclosed technique a smaller sized battery, which is rechargeable, can be used in an ICD can in order to significantly extend the lifespan of the rechargeable ICD. An immediate benefit of such an ICD is that the number of times the rechargeable ICD can needs to be replaced is substantially reduced as compared with known ICD cans that are replaced every 5-7 years. According to the disclosed technique, rechargeable ICD can 140 may need to be replaced every 10-15 years.

Figure 4A:
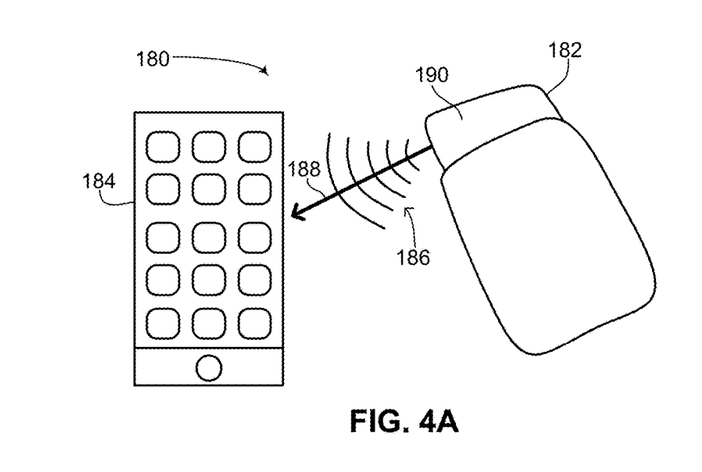
FIG. 4A is a schematic illustration of the rechargeable ICD of FIG. 2A communicating with a smartphone, constructed and operative in accordance with another embodiment of the disclosed technique.

Reference is now made to FIG. 4A, which is a schematic illustration of the rechargeable ICD of FIG. 2A communicating with a smartphone, generally referenced 180, constructed and operative in accordance with another embodiment of the disclosed technique. As in FIGS. 2B and 3, the at least one lead of the rechargeable ICD is not shown so as to keep the figure less cluttered. As shown, a rechargeable ICD can 182 can communicate signals wirelessly to an external device 184. External device 184 may be a smartphone, tablet computer, personal digital assistant and the like. External device 184 is a user device. As shown, wireless signals 186 are transmitted from a non-active portion 190 of rechargeable ICD can 182. Wireless signals 186 can be transmitted using known wireless protocols such as Bluetooth®, Bluetooth low energy (BLED), Wi-Fi®, Medical Implant Communication Service (MICS), Medical Implant Communication Service Medical Data Service (MICS/MEDS), Medical Device Radiocommunications Service (MedRadio) and the like. External device 184 may belong to the patient or a relative of the patient. As shown by an arrow 188, communication from rechargeable ICD can 182 to external device 184 is unidirectional. This may be for security purposes to not compromise control of the processor (not shown) in rechargeable ICD can 182, which may only be modified or given instructions via a unique programmer (not shown) which may be located at the office of the physician of the patient. External device 184 may include an application (not shown) for displaying various parameters of the rechargeable ICD. The information provided to external device 184 may include status indicators of the rechargeable ICD as well as data about the patient garnered from a sensor (not shown) on a lead (not shown) of the rechargeable ICD. As mentioned above in FIG. 3, a dedicated antenna in the rechargeable ICD of the disclosed technique may be used solely for transmitting and communicating status information to a patient via wireless protocols such as BLED, Wi-Fi® or other known wireless communication methods.

Figure 4B:
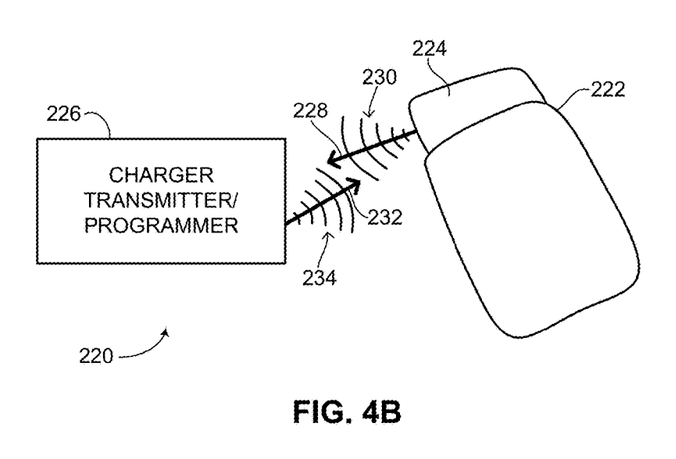
FIG. 4B is a schematic illustration of the rechargeable ICD of FIG. 2A communicating with a charger transmitter/programmer, constructed and operative in accordance with a further embodiment of the disclosed technique.

Reference is now made to FIG. 4B, which is a schematic illustration of the rechargeable ICD of FIG. 2A communicating with a charger transmitter/programmer, generally referenced 220, constructed and operative in accordance with a further embodiment of the disclosed technique. As in FIG. 4A, the at least one lead of the rechargeable ICD is not shown so as to keep the figure less cluttered. As shown, a rechargeable ICD can 222 can communicate signals wirelessly with a charger transmitter/programmer 226. Charger transmitter/programmer 226 is a physician's device for inductively charging the rechargeable ICD as well as providing instructions and signals for modifying and programming the processor (not shown) of the rechargeable ICD. As shown, high energy wireless signals 230 and 234 are transmitted from and received to a non-active portion 224 of rechargeable ICD can 222. High energy wireless signals are required in order to recharge the battery of the rechargeable ICD quickly and efficiently. Wireless signals 230 and 234 can be transmitted using known high energy wireless protocols such as RF energy and the like. As shown by arrows 228 and 232, communication from rechargeable ICD can 222 to charger transmitter/programmer 226 is bidirectional. Charger transmitter/programmer 226 can transmit energy to inductively charge the battery (not shown) in rechargeable ICD can 222. The energy used to recharge the battery can also be modulated. The modulated signals can thus be used to transmit programming instructions to the processor (not shown) in rechargeable ICD can 222. Likewise, rechargeable ICD can 222 can transmit diagnostic information to charger transmitter/programmer 226 which a physician can use to determine if changes need to be made to the functioning of rechargeable ICD can 222 via its processor (not shown). The diagnostic information can include electrocardiogram information about the patient's heart, other monitored parameters of the patient's heart gathered from the sensor (not shown) on the at least one lead (also not shown) of the rechargeable ICD, as well as information about the rechargeable ICD such as how many electrical shocks were delivered over the past year, how much charge is left on the battery, when charging is required and the like.

It is noted that the rechargeable ICD of the disclosed technique is designed to store about twenty electrical shocks, which should be sufficient for a year's worth of functioning. In this respect, the rechargeable ICD of the disclosed technique is to be recharged once a year. The battery of the rechargeable ICD can be recharged at a physician's office in about an hour, thus not tremendously inconveniencing a patient having such an ICD in their heart. It is also noted that charger transmitter/programmer 226 may include a touchscreen (not shown) or a plurality of buttons (not shown) for programming the rechargeable ICD.

It is further noted that as mentioned above, the rechargeable ICD of the disclosed technique includes an active portion and a non-active portion. According to a preferred embodiment of the disclosed technique, when the rechargeable ICD is implanted inside a patient, whether it be near the clavicle bone, around the fifth rib in the ribcage or adjacent to the ribcage, or any other position in the thoracic region of the patient, the active portion of the rechargeable ICD should be placed proximal to the heart of the patient whereas the non-active portion of the rechargeable ICD should be placed proximal to the skin of the patient. In this respect, the non-active portion is placed subcutaneously as close as possible to the surface of the skin in order to minimize the distance between charger transmitter/programmer 226 and the induction antenna (not shown) in the rechargeable ICD. The efficiency at which the induction antenna can receive energy wirelessly and thus pass on the energy to recharge the rechargeable battery of the rechargeable ICD is directly proportional to the distance between the induction antenna and the charger transmitter/programmer 226. Charger transmitter/programmer 226 may include a lead (not shown) fashioned as a suction cup which can be placed on the skin of the patient directly above the non-active portion of the rechargeable ICD. By minimizing the distance between the non-active portion and the aforementioned lead, efficient wireless inductive charging of the rechargeable battery of the rechargeable ICD can be achieved. According to the disclosed technique, the rechargeable ICD can be placed in any position in the thoracic region of the patient as well as the ribcage, the back or the belly, however as the distance between the non-active portion and the charger transmitter/programmer 226 increases, more time and possibly more energy will be required to recharge the rechargeable battery of the rechargeable ICD. An increase in energy may result in an increase in the temperature of the skin tissue and cells near the rechargeable ICD, which may cause tissue and cell damage if the temperature increase is too great.

Figure 5:
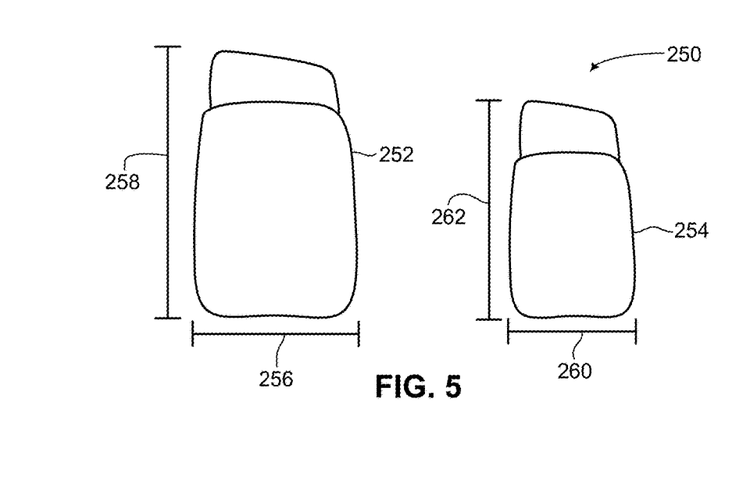
FIG. 5 is a schematic illustration showing a difference in size between the ICDs of FIGS. 1A, 1B and 1D and the rechargeable ICD of FIG. 2A, constructed an operative in accordance with another embodiment of the disclosed technique.

Reference is now made to FIG. 5, which is a schematic illustration showing a difference in size between the ICDs of FIGS. 1A, 1B and 1D and the rechargeable ICD of FIG. 2A, generally referenced 250, constructed an operative in accordance with another embodiment of the disclosed technique. A prior art ICD can 252 is shown, having a width 256 and a length 258. Next to prior art ICD can 252 is a rechargeable ICD can 254, constructed according to the disclosed technique. Rechargeable ICD can 254 is shown having a width 260 and a length 262. As can be seen, rechargeable ICD can 254 is substantially smaller than prior art ICD can 252 due to the smaller size of a rechargeable battery (not shown) used in rechargeable ICD can 254. This can lead to a more comfortable ICD can in the subcutaneous area in the patient where the ICD can is implanted.

The disclosed technique has been described above as relating to a rechargeable ICD having a can and lead design. It is noted that the disclosed technique can also apply to other ICD designs, such as subcutaneous ICDs which only have a housing or can but no external leads. In such ICDs, the active section of the can acts as an electrode for applying a high voltage shock to the heart of a patient. In addition, the disclosed technique has been described as having a can comprising an active section and a non-active section, with the at least one antenna being placed in the non-active section. According to another embodiment of the disclosed technique, the can of the rechargeable ICD is completely active and does not include a non-active section as shown above in FIG. 2B. In this embodiment, the at least one antenna (not shown) is placed internally within the can which is an active section. The at least one antenna will still be able to transmit and receive signals through the active section although a higher energy level might be needed to transmit and receive signals and for the at least one antenna to receive enough energy to inductively recharge the battery. According to a further embodiment, the can of the rechargeable ICD is completely active and does not include a non-active section as shown above in FIG. 2B and includes at least one antenna which is placed on the outer surface of the active can. The at least one antenna couples with components inside the active can via a dielectric feed-thru on the surface of the active can.

Figure 6A:
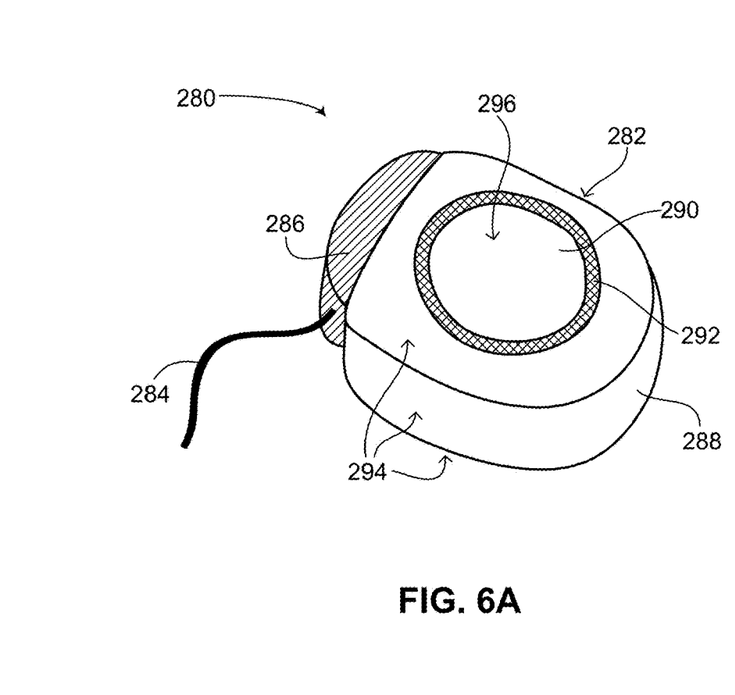
FIG. 6A is a schematic illustration another rechargeable ICD, constructed an operative in accordance with a further embodiment of the disclosed technique.

Reference is now made to FIG. 6A, which is a schematic illustration another rechargeable ICD, generally referenced 280, constructed an operative in accordance with a further embodiment of the disclosed technique. Rechargeable ICD 280 has a general D-shape and includes a can 282 and at least one lead 284. Can 282 is a hermetically sealed can. Can 282 includes an active section 288 and a non-active section 290. As shown, active section 288 covers most of the surface area of can 282. Active section 288 can act as an electrode with at least one lead 284 to form an electric shock vector for applying a high voltage shock to the heart (not shown) of a patient. Active section 288 can also act as a sensor for sensing electrical activity of the heart. The active areas of can 282 are shown by a plurality of arrows 294. Non-active section 290 has a substantially circular shape and substantially acts as an antenna (not shown) for transmitting and receiving information wirelessly while also receiving RF energy to inductively charge the rechargeable battery of ICD 280. Non-active section 290 may also house at least one antenna (not shown). The non-active area of can 282 is shown by an arrow 296. Non-active section 290 is insulated electrically from active section 288 by an isolator 292. Isolator 292 has a substantially circular shape, can be made from insulating materials such as glass, ceramic and the like and electrically insulates non-active section 290 from active section 288. Isolator 292 can be a glass metal ceiling. Isolator 292 may include a dielectric feed-thru (not shown) for coupling non-active section 290 with active section 288 such that EM energy received by non-active section 290 can be passed to active section 288 while nevertheless keeping it electrically insulated from active section 288. Non-active section 290 may be coupled with any of the internal components of can 282, such as at least one high voltage capacitor (not shown), a charging circuit (not shown), an electronic circuit (not shown) and a rechargeable power source (not shown). Can 282 also includes a lead connector 286, for coupling at least one lead 284 with the internal components of active section 288. As explained above, active section 288 includes all the necessary components for the functioning of rechargeable ICD 280 such as at least one high voltage capacitor, an electronic circuit, a charging circuit and a rechargeable power source. Lead connector 286 may be coupled with active section 288 via another dielectric feed-thru (not shown).

Figure 6B:
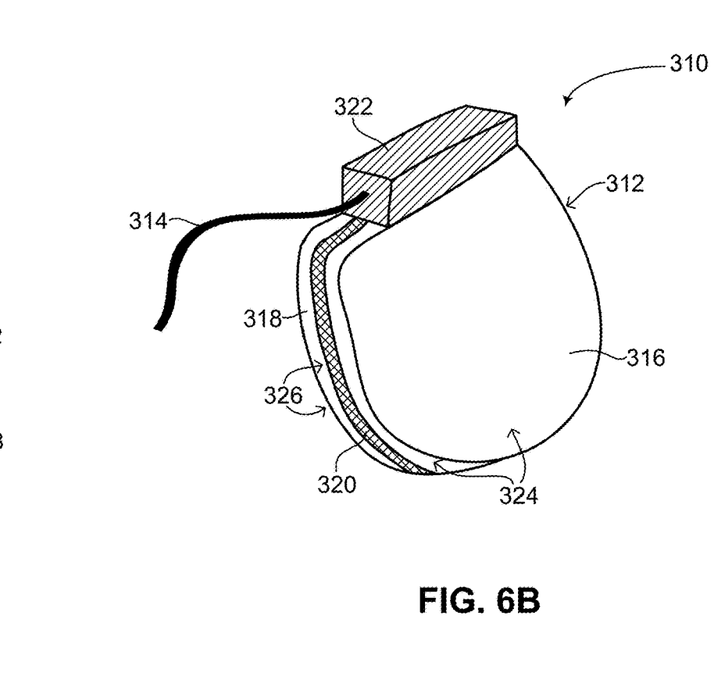
FIG. 6B is a schematic illustration a further rechargeable ICD, constructed an operative in accordance with another embodiment of the disclosed technique.

Reference is now made to FIG. 6B, which is a schematic illustration a further rechargeable ICD, generally referenced 310, constructed an operative in accordance with another embodiment of the disclosed technique. Rechargeable ICD 310 has a general D-shape and includes a can 312 and at least one lead 314. Can 312 is a hermetically sealed can. Can 312 includes an active section 318 and a non-active section 316. As shown, active section 318 and non-active section 316 each substantially cover about half the surface area of can 312. Both non-active section 316 and active section 318 have substantially D-shapes. Active section 318 can act as an electrode with at least one lead 314 to form an electric shock vector for applying a high voltage shock to the heart (not shown) of a patient. Active section 318 can also act as a sensor for sensing electrical activity of the heart. The active areas of can 312 are shown by a plurality of arrows 326 whereas the non-active areas of can 312 are shown by a plurality of arrows 324. Non-active section 316 substantially acts as an antenna (not shown) for transmitting and receiving information wirelessly while also receiving RF energy to inductively charge the rechargeable battery of ICD 310. Non-active section 316 may also house at least one antenna (not shown). Non-active section 316 is insulated electrically from active section 318 by an isolator 320. Isolator 320 has a substantially circular shape and separates the active half of can 312 from the non-active half of can 312. The separation of isolator 320 can be along the circumference of can 312. The separation of isolator 320 can also substantially divide can 312 into two, active section 318 and non-active section 316. Isolator 320 can be made from insulating materials such as glass, ceramic and the like and electrically insulates non-active section 316 from active section 318. Isolator 320 can be a glass metal ceiling. Isolator 320 may include a dielectric feed-thru (not shown) for coupling non-active section 316 with active section 318 such that EM energy received by non-active section 316 can be passed to active section 318 while nevertheless keeping it electrically insulated from active section 318. Can 312 also includes a lead connector 322, for coupling at least one lead 314 with the internal components of active section 318. As explained above, active section 318 includes all the necessary components for the functioning of rechargeable ICD 310 such as at least one high voltage capacitor (not shown), an electronic circuit (not shown), a charging circuit (not shown) and a rechargeable power source (not shown). Non-active section 316 may be coupled with the internal components of can 312 as listed above, such as at least one high voltage capacitor, a charging circuit, an electronic circuit and a rechargeable power source. Lead connector 322 may be coupled with active section 318 via another dielectric feed-thru (not shown).

It will be appreciated by persons skilled in the art that the disclosed technique is not limited to what has been particularly shown and described hereinabove. Rather the scope of the disclosed technique is defined only by the claims, which follow.

The invention claimed is:
1. Rechargeable implantable cardioverter defibrillator (ICD) comprising:
   a hermetically sealed can; and
   at least one lead, coupled with said hermetically sealed can,
   said hermetically sealed can comprising:
      at least one high voltage capacitor;
      an electronic circuit, coupled with said at least one high voltage capacitor; and
      a rechargeable battery, coupled with said electronic circuit and said at least one high voltage capacitor;
   an outer surface of said hermetically sealed can comprising:
      an active section; and
      a non-active section, said non-active section being electrically insulated from said active section,
   wherein a surface area of said active section acts as at least one of an electrode with said at least one lead for forming an electric shock vector for applying a high voltage shock and a sensor for sensing electrical activity;
   wherein a surface area of said non-active section acts as at least one antenna for transmitting and receiving information wirelessly while also receiving electromagnetic (EM) energy to inductively charge said rechargeable battery; and
   wherein when implanted inside a patient, said active section is placed proximal to the heart of said patient and said non-active section is placed proximal to the skin of said patient.

2. The rechargeable ICD according to claim 1, wherein said electronic circuit comprises a processor.

3. The rechargeable ICD according to claim 1, wherein said electronic circuit comprises a charging circuit, coupled with said rechargeable battery.

4. The rechargeable ICD according to claim 1, wherein said at least one lead is placed in a location in a patient selected from the list consisting of:
   intravascularly; and
   nonvascularly.

5. The rechargeable ICD according to claim 1, said hermetically sealed can further comprising a dielectric feed-thru, for coupling said at least one lead with at least one of said at least one high voltage capacitor, said electronic circuit and said rechargeable battery.

6. The rechargeable ICD according to claim 1, said hermetically sealed can further comprising a lead connector, for coupling said at least one lead with at least one of said at least one high voltage capacitor, said electronic circuit and said rechargeable battery.

7. The rechargeable ICD according to claim 1, wherein said non-active section is made from an insulating material selected from the list consisting of:
   glass;
   ceramic; and
   porcelain.

8. The rechargeable ICD according to claim 1, wherein said at least one antenna is internal to said non-active section.

9. The rechargeable ICD according to claim 1, wherein said at least one antenna comprises a transmission antenna and an induction antenna.

10. The rechargeable ICD according to claim 9, wherein said transmission antenna and said induction antenna are coupled with said electronic circuit and wherein said induction antenna is also coupled with a charging circuit in said active section.

11. The rechargeable ICD according to claim 10, wherein said induction antenna receives EM energy and wherein said charging circuit converts said received EM energy into electrical energy for inductively recharging said rechargeable battery.

12. The rechargeable ICD according to claim 9, wherein said transmission antenna only transmits signals and wherein said induction antenna transmits and receives signals.

13. The rechargeable ICD according to claim 1, wherein said rechargeable battery is a lithium-ion battery.

14. The rechargeable ICD according to claim 1, wherein said received signals and said transmitted signals are wireless protocol signals.

15. The rechargeable ICD according to claim 14, wherein said wireless protocol signals are selected from the list consisting of:
- Bluetooth®;
- Bluetooth low energy (BLE®);
- Wi-Fi®;
- Medical Implant Communication Service (MICS);
- Medical Implant Communication Service Medical Data Service (MICS/MEDS); and
- Medical Device Radiocommunications Service (MedRadio).

16. The rechargeable ICD according to claim 1, wherein said at least one antenna can wirelessly transmit signals indicative of a status of said rechargeable ICD to an external device; and
wherein said at least one antenna can wirelessly receive signals from a programmer for programming said electronic circuit.

17. The rechargeable ICD according to claim 16, wherein said received signals from said programmer are modulated signals for simultaneously recharging said rechargeable battery and programming said electronic circuit.

18. Rechargeable implantable cardioverter defibrillator (ICD) comprising:
a hermetically sealed can; and
at least one lead, coupled with said hermetically sealed can,
said hermetically sealed can comprising:
at least one high voltage capacitor;
an electronic circuit, coupled with said at least one high voltage capacitor; and
a rechargeable battery, coupled with said electronic circuit and said at least one high voltage capacitor;
an outer surface of said hermetically sealed can comprising:
an active section;
a non-active section; and
an isolator, coupled with said active section and said non-active section, for electrically insulating said active section from said non-active section,
wherein a surface area of said active section acts as at least one of an electrode with said at least one lead for forming an electric shock vector for applying a high voltage shock and a sensor for sensing electrical activity;
wherein a surface area of said non-active section acts as at least one antenna for transmitting and receiving information wirelessly while also receiving electromagnetic (EM) energy to inductively charge said rechargeable battery; and
wherein said isolator is made from an insulating material.

19. The rechargeable ICD according to claim 18, wherein said hermetically sealed can has a D-shape.

20. The rechargeable ICD according to claim 18, wherein said non-active section has a substantially circular shape.

21. The rechargeable ICD according to claim 18, wherein said isolator has a circular shape.

22. The rechargeable ICD according to claim 18, wherein each of said active section and said non-active section has a D-shape, separating said outer surface of said hermetically sealed can into an outer active half of said hermetically sealed can and an outer non-active half of said hermetically sealed can;
wherein said isolator has a circular shape; and
wherein said isolator separates said outer active half from said outer non-active half.

23. The rechargeable ICD according to claim 22, wherein said isolator is along a circumference of said hermetically sealed can.

24. Rechargeable implantable cardioverter defibrillator (ICD) comprising:
an active section; and
a non-active section, said non-active section being electrically insulated from said active section and forming a hermetically sealed can with said active section,
said active section comprising:
at least one high voltage capacitor;
an electronic circuit, coupled with said at least one high voltage capacitor; and
a rechargeable battery, coupled with said electronic circuit and said at least one high voltage capacitor;
wherein a surface area of said active section acts as at least one of an electrode for forming an electric shock vector for applying a high voltage shock and a sensor for sensing electrical activity;
wherein a surface area of said non-active section acts as at least one antenna for transmitting and receiving information wirelessly while also receiving electromagnetic (EM) energy to inductively charge said rechargeable battery; and
wherein when implanted inside a patient, said active section is placed proximal to the heart of said patient and said non-active section is placed proximal to the skin of said patient.

25. Rechargeable implantable cardioverter defibrillator (ICD) comprising:
a hermetically sealed can; and
at least one lead, coupled with said hermetically sealed can,
said hermetically sealed can comprising:
at least one high voltage capacitor;
an electronic circuit, coupled with said at least one high voltage capacitor;
a rechargeable battery, coupled with said electronic circuit and said at least one high voltage capacitor;
at least one antenna; and
a dielectric feed-thru,
wherein said at least one antenna can wirelessly receive electromagnetic (EM) energy for inductively charging said rechargeable battery;
wherein said at least one antenna can wirelessly transmit signals indicative of a status of said rechargeable ICD to an external device;
wherein said at least one antenna can wirelessly receive signals from a programmer for programming said electronic circuit; and
wherein said at least one antenna is placed on an outer surface of said hermetically sealed can and is coupled with said electronic circuit and said rechargeable battery via said dielectric feed-thru.

26. The rechargeable ICD according to claim 18, wherein said insulating material is selected from the list consisting of:
- glass;
- ceramic; and
- porcelain.

* * * * *